(12) United States Patent
Westmeyer et al.

(10) Patent No.: US 6,590,117 B1
(45) Date of Patent: Jul. 8, 2003

(54) PROMOTED HYDROSILATION REACTIONS

(75) Inventors: Mark D. Westmeyer, Marietta, OH (US); Melinda B. Hale, Belmont, WV (US); R. Shawn Childress, Marietta, OH (US); Michelle A. Filipkowski, Marietta, OH (US); Rodica S. Himmeldirk, Vincent, OH (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/004,156

(22) Filed: Nov. 15, 2001

(51) Int. Cl.$^7$ .................................................. C07F 7/04
(52) U.S. Cl. ....................................................... 556/479
(58) Field of Search ......................................... 532/479

(56) References Cited

U.S. PATENT DOCUMENTS

| | | |
|---|---|---|
| 2,971,970 A | 2/1961 | Bluestein et al. |
| 3,925,434 A | 12/1975 | Chuang |
| 4,292,434 A | 9/1981 | Lindner et al. |
| 4,417,069 A * | 11/1983 | Brown ........................ 556/479 |
| 4,481,364 A | 11/1984 | Chu et al. |
| 4,584,361 A | 4/1986 | Janik et al. |
| 4,614,812 A | 9/1986 | Schilling, Jr. |
| 4,804,768 A | 2/1989 | Quirk et al. |
| 4,966,981 A | 10/1990 | Takai et al. |
| 5,103,033 A | 4/1992 | Bank |
| 5,191,103 A | 3/1993 | Mehta et al. |
| 5,283,348 A | 2/1994 | Bank |
| 5,359,111 A | 10/1994 | Kleyer et al. |
| 5,359,112 A * | 10/1994 | Drake ........................ 556/479 |
| 5,391,676 A | 2/1995 | Eckberg et al. |
| 5,623,083 A | 4/1997 | Bank et al. |
| 5,663,400 A | 9/1997 | Reitmeier et al. |
| 5,756,795 A | 5/1998 | Bank et al. |

FOREIGN PATENT DOCUMENTS

RU 415268 7/1974

OTHER PUBLICATIONS

Comprehensive Handbook on Hydrosilation; edited by B. Marciniec, Ed.; Pergamon Press, New York (1992); Ch.4; pp 160–170 "The Effect of Substituents at Silicon on the Reactivity of the Si–H Bond in Hydrosilylation".

"Homogeneous Catalysis of Hydrosilation by Transition Metals" by John L. Speier, appearing in Advantages in Organometallic Chemistry. vol. 17. pp. 407–447. (1979).

"The Mechanism of the Addition of Hydrogenodichlorosilanes to Acrylonitrile" by Z.V. Belyakova et al. Translated from Zhurnal Obshchei Khimii, vol. 34, No. 5, pp. 1480–1484 (May 1964).

Latest Research on the Hydrosilylation by E. Lukevics. Russian Chemical Reviews. 46 (3), (1977).

CA Selects: Organosilicon Chemistry. Issue 18 (1989) at p. 8. 111: 78085m Studies on Hydrosilylation of Allyl Chloride Catalyzed by Chloroplatinic Acid–Amine Systems. C. Hu et al. *Fenzi Cuihua*, 1988, 2, 38–43; see Chem.Abstr. 1989, 111, 78085m).

Chemical Abstracts: Hydrocarbons Containing Silicon. vol. 60, col. 3008. Th. Goldschmidt by Goetz Koerner et al. (1963).

* cited by examiner

Primary Examiner—Samuel Barts
(74) Attorney, Agent, or Firm—Michael P. Dilworth

(57) ABSTRACT

A process of preparing compounds containing silicon-carbon bonds by the hydrosilation of a hydridoalkoxysilyl reactant with an olefinic reactant comprises operating the process in the presence of a platinum catalyst and a reaction promoter comprising a weakly nucleophilic amine of the formula $NZ^1Z^2Z^3$ wherein $Z^1$ is an aryl, alkaryl, or aralkyl group of $C_6$ to $C_{20}$ carbon atoms, or an organosilyl substituent, $SiR_3$, wherein R is an alkyl of $C_1$ to $C_{20}$ or an aryl of $C_6$ to $C_{10}$, $Z^2$ is hydrogen, alkyl of $C_1$ to $C_{20}$, an aryl, alkaryl, or aralkyl group of $C_6$ to $C_{20}$ carbon atoms or $SiR_3$, wherein R is as previously defined; $Z^3$ is the same as $Z^1$ or $Z^2$, and, optionally, two Of $Z^1$, $Z^2$ and $Z^3$ taken together with the nitrogen atom form an aromatic heterocyclic ring.

15 Claims, No Drawings

PROMOTED HYDROSILATION REACTIONS

BACKGROUND OF THE INVENTION

In the production of silicon compositions, transition metal catalysts have long been known to promote the hydrosilation reaction. Each transition metal-catalyzed hydrosilation reaction differs dramatically such that it is difficult to predict which transition metal will efficiently catalyze the hydrosilation reaction of a specific hydridosilyl reactant with a particular unsaturated reactant. For example, the effect of substituents on the silicon atom on adduct yield obtained in the platinum (Pt)-catalyzed reactions with 1-alkenes is in the following order of activity (R=Et):

$$Cl_3SiH > Cl_2RSiH > (RO)_3SiH > (RO)_2RSiH > R_3SiH$$

The general trend for Pt-catalyzed hydrosilation reactions is that chlorosilanes are more reactive than alkoxysilanes (*Comprehensive Handbook on Hydrosilylation*; B. Marciniec, Ed.; Pergamon Press, New York, 1992; Ch.4; J. L. Speier Adv. Organomet. Chem. 1979, 17, 407; E. Lukevics *Russ. Chem. Rev.* 1977, 46, 197). However, if one evaluates a different transition metal or olefin, the above trend may be different. For example, in the hydrosilation reaction of heptene with rhodium (Rh), the above trend is the reversed. Due to the relative importance of the Pt-catalyzed hydrosilation reaction in commercial production of organofunctional silanes, a process that improved both the reactivity and selectivity of alkoxysilanes in the hydrosilation relative to that seen with chlorosilanes would be valuable.

A number of patents in the art have disclosed that various promoters can increase the rates and/or selectivities of hydrosilation reactions. In terms of chemical structures or properties, the various types of promoters differ dramatically, such that it is not possible to predict which chemical structures or properties are important for promotion, or even which hydrosilation reactions may be promoted, since promotion will also depend on the chemical structures and properties of each of the hydridosilyl reactant, the unsaturated reactant, and the hydrosilation catalyst. For example, the reaction of trichlorosilane with allyl chloride is promoted by weak amines such as phenothiazine (V. T. Chuang U.S. Pat. No. 3,925,434), while the reaction of methyldichlorosilane with allyl chloride requires a more basic tertiary amine such as tributylamine (Ger. Patent 1,156,073; C. Hu et al. *Fenzi Cuihua*, 1988, 2, 38–43; see Chem. Abstr. 1989, 111, 78085 m). Both of those reactions can be promoted with a second hydridosilane (U.S. Pat. No. 4,614,812) through a different promotion mechanism. Alkali metal carbonates or bicarbonates promote hydrosilations of allylic amines with hydridoalkoxysilanes (U. S. Pat. No. 4,481,364). Other hydrosilation reactions are promoted by phosphines, oxygen gas (D. L. Kleyer et al. U.S. Pat. No. 5,359,111), oxygen-containing organics including aldehydes, unsaturated ketones (R. Reitmeier et al. U.S. Pat. No. 5,663,400, H. M. Bank et al. U.S. Pat. No. 5,623,083), tertiary alcohols and silylated derivatives thereof, and propargylic alcohols and silylated derivatives thereof (H. M. Bank et al. U.S. Pat. No. 5,756,795), inorganic or organic salts including sodium alkoxides and compounds of tin and cobalt, and other organic compounds, including alcohols, diols, ethers and esters. Carboxylic acids, along with ketones, and esters thereof, appear to promote platinum-catalyzed hydrosilation reactions between hydridoalkoxysilanes and allylamine (U.S. Ser. No. 415,268). The use of acetic acid in promoting hydrosilations involving trimethoxysilane has been coincidental with the use of vinylcyclohexene oxide as the olefin, since acetic acid was discovered to be an impurity derived from early processes to make that epoxyolefin using peracetic acid (U.S. Pat. No. 2,687,406), as well as allyl glycidyl ether *j. Am. Chem. Soc.* 1959, 81, 3350).

Hydrosilation promotion effects are narrowly specific, and an effective promoter may work for a single hydrosilation reaction between a specific hydridosilane and a specific olefin. In addition to increasing reaction rates, yields, or selectivities, a promoter may act by preventing undesirable side reactions, which reduce yields/selectivities, such as undesired polymerization or formation of less desirable isomeric products. For example, added methanol is disclosed as being effective in reducing the undesired beta-isomer content in reaction products from platinum-catalyzed hydrosilations between trimethoxysilane and the epoxyolefins, i.e., vinylcyclohexene monoepoxide and allyl glycidyl ether (H. Takai et al. U.S. Pat. No. 4,966,981).

The use of amines in the hydrosilation of hydridosilane and acrylonitrile has been reported extensively, particularly tertiary amines in the presence of copper (Cu) (B. A. Bluestein U.S. Pat. No. 2,971,970, 1961; Z. V. Belyakova et al. translation from Zhurnal Obshchei Khimii 1964, 34, 1480–1484; A. Rajkumar et al. *Organometallics* 1989, 8, 549–550; H. M. Bank U.S. Pat. No. 5,283,348, and U.S. Pat. No. 5,103,033). U.S. Pat. No. 4,292,434 (T. Lindner et al.) describes the preparation of an amine-platinum catalyst and its use in the hydrosilation reaction. K. R. Mehta et al. in U.S. Pat. No. 5,191,103 reported the use of sterically hindered amines, phosphines or their equivalent salts in the presence of a platinum catalyst to promote the hydrosilation reaction.

In addition to promoting the hydrosilation reaction, amines have been reported to be inhibitors for the hydrosilation reaction. For example G. Janik et al. in U.S. Pat. No. 4,584,361 reported that amines inhibited polyorganosiloxane compositions at temperatures below 40° C., but not at 135° C. Also R. P. Eckberg et al. reported the use of tertiary amines in the presence of both Rh and Pt catalysts to inhibit epoxy-polymerization in the production of epoxysilicones.

The hydrosilation reactions of many olefins, particularly amino-functional olefins, are either too slow or do not occur. For those olefins that do undergo hydrosilation, formation of the undesired β-isomer is a competing side reaction. The type of silane employed also impacts the rate of reaction. Typically, sluggish hydrosilation reactions result in an increase of the competing side-reactions, e.g., olefin isomerization or polymerization. Accordingly, a process which improves the reactivity and selectivity of the transition metal-catalyzed hydrosilation reactions of olefins continues to be a commercially desirable objective.

SUMMARY OF THE INVENTION

In accordance with the invention, a process is provided which comprises reacting (a) hydridoalkoxysilane with (b) olefin in the presence of (c) platinum catalyst and (d) a weakly nucleophilic amine of the formula $NZ^1Z^2Z^3$, wherein $Z^1$ is an aryl, alkaryl, or aralkyl group of $C_6$ to $C_{20}$ carbon atoms, or an organosilyl group of the formula $SiR_3$, wherein R is alkyl of $C_1$ to $C_{20}$ or aryl of $C_6$ to $C_{10}$; $Z^2$ is hydrogen, alkyl of $C_1$ to $C_{20}$, an aryl, alkaryl, or aralkyl group of $C_6$ to $C_{20}$, or $SiR_3$, wherein R is as previously defined; $Z^3$ is the same as $Z^1$ or $Z^2$; and optionally two of $Z^1$, $Z^2$ and $Z^3$ taken together with the nitrogen atom form an aromatic heterocyclic ring. The process of the invention exhibits improved yields and selectivities with respect to the desired reaction products.

DETAILED DESCRIPTION OF THE INVENTION

This invention provides a process for improving the yields and rates of the hydrosilation of alkoxyhydridosilane under relatively mild conditions using a weakly nucleophilic amine in the presence of a hydrosilation catalyst.

AMINES

Weakly nucleophilic amines containing substituents capable of π-interation with the amine's lone pair of electrons such as aromatic or silicon-substituents can be employed in the practice of this invention. Thus, weakly nucleophilic amine promoters possess the general formulae $NZ^1Z^2Z^3$ wherein $Z^1$ is an aryl, alkaryl, or aralkyl group of six to twenty carbon atoms, or an organosilyl group of the formula $SiR_3$, wherein R is an alkyl of $C_1$ to $C_{20}$, preferably $C_1$ to $C_4$, or aryl of $C_6$ to $C_{10}$; $Z^2$ is hydrogen, alkyl of $C_1$ to $C_{20}$, preferably $C_1$ to $C_4$, an aryl, alkaryl, or aralkyl group of $C_6$ to $C_{20}$, or $SiR_3$ wherein R is as previously defined; and $Z^3$ is the same as $Z^1$ or $Z^2$. Optionally, two of $Z^1$, $Z^2$ and $Z^3$ taken together may form an aromatic heterocyclic ring including the nitrogen atom. Weakly nucleophilic amines include, but are not limited to, aniline, hexamethyldisilazane, phenothiazine, aminonaphthalene, benzylamine, pyridine and their corresponding derivatives. Aniline, benzylamine, and hexamethyldisilazane are the preferred amines with this invention, the choice depending on the hydridosilane and olefin reactants.

HYDRIDOSILANES

Promotable hydridosilanes in general can be represented by the formula $R_nX_{3-n}SiH$, wherein R is a branched or linear alkyl group of 1 to 18 carbon atoms, a cyclic alkyl group of four to eight carbon atoms or an aryl, alkaryl, or aralkyl group of six to twelve carbon atoms, optionally containing halogen, oxygen or nitrogen substituents with the proviso that such substituents do not interfere with either hydrosilation or promotion, and X is an alkoxy group, selected from -OR, wherein R is as defined above, and n is 0, 1, or 2. The hydridosilanes may be alkoxysilanes selected from the group of trimethoxysilane, triethoxysilane, tri-n-propoxysilane, and triisopropoxysilane. Trimethoxysilane and triethoxysilane are preferred. Other hydridoalkoxysilanes include alkylalkoxysilanes such as methyldimethoxysilane, methyldiethoxysilane, dimethylmethoxysilane, and dimethylethoxysilane.

OLEFINS

The olefins which can be employed in accordance with the invention are aliphatically unsaturated molecules, which may have certain functional substituents thereon. The term "olefins" utilized herein is being used in its broadest sense and therefore shall be understood to include alkenes, vinyl group-containing and allyl group-containing compounds. Terminal alkenes can be advantageously employed, such as the 1-alkenes, including ethylene, propylene, butene, pentene, hexene, octene, hexadecene, octadecene, trivinylcyclohexene, and the 2-alkyl-1-alkenes, such as 2-methylpropene, 2-methylbutene, diisobutylene, as well as non-terminal alkenes such as tertiary amylene and 2-butene. The 1-alkenes are preferred. Other suitable olefins include the epoxy olefins, such as vinylcyclohexene monoxide, allyl glycidyl ether, and allylic olefins, including, but not limited to allyl esters, allyl polyethers, and allylic tertiary amines, as well as their methallyl derivatives. Other olefins include the amino olefins, such as N-allylaniline, N,N-dimethallylamine, and N-ethylmethallylamine. Vinyl group-containing compounds include the vinyl esters and ethers, vinylsilanes, acrylates and methacrylates.

CATALYST

Catalysts include those which contain platinum and that function as either homogeneous or heterogeneous hydrosilation catalysts. Typical catalysts include chloroplatinic acid and various solutions thereof, including solutions wherein the chloroplatinic acid has been chemically modified, chloroplatinate salts and their solutions, vinylsiloxane complexes containing platinum and solutions thereof (Karstedt catalyst), olefin and diolefin complexes of platinum and solutions thereof, and platinum deposited as the metal on various substrates, including carbon, alumina, silica, organically modified silicas, or base metals. Platinum complexes containing strongly bound ligands such as phosphines, acetylacetonate groups, or amines, may be promotable with the proviso that such ligands must not interfere with either the hydrosilation or the promotion. The catalyst should be used at a level of 0.5 to 100 ppm based on total charge, preferably 5 to 50 ppm, most preferably 5 to 15 ppm.

PROCESS

Promotion by amines is not subject to limitations regarding equipment, relative to size or type of material of construction. A wide variety of laboratory or commercial scale equipment currently capable of running hydrosilation reactions may be used. The hydrosilation process may be run in a batch, semi-batch or continuous mode.

Reaction conditions are also not narrowly critical with regard to temperature, pressure, or the absence or presence of inert solvents. Conditions currently in use for various hydrosilation reactions can be used for the promoted hydrosilations. It is possible that effective promotion will be accompanied by the added advantages of lowering reaction temperature, and catalyst concentration, or both. Preferred reaction conditions include a temperature from about ambient temperature up to about 150° C. with 60 to 120° C. being most preferred. Generally, the process is carried out at a pressure of about 0.2 to 2.0 atmospheres (0.02–0.2 MPa), with ambient pressure being preferred, but operation at higher or lower pressures may be performed to maintain higher or lower reaction temperatures dependent on the volatilities of the respective reactants.

The residence time within the reactor is not critical but should be sufficient to achieve a satisfactory degree of conversion to the hydrosilated product, i.e., >80%, within acceptable limits given the volume of the equipment and the desired rate of production. Typical acceptable residence times are on the order of 0.5 to 4 hours.

Preferably the olefin should be present at a molar excess of 5–20%, though a stoichiometric equivalence or a molar excess of the silane may be used. The use of promoters of the instant invention can allow the use of lower molar excesses of olefins due to reduction of the competing olefin isomerization side-reaction.

The amine may be present at the start of the hydrosilation, or may be added during the reaction if it is not proceeding well(Caution—amine should not be added to incomplete reactions wherein significant quantities of both hydridosilyl reactant and olefinic reactant have accumulated, a rapid exothermic reaction may occur). The amines can be used at a concentration of 25 to 20,000 ppm (wt/wt); however, the preferred amine concentration is dependent on the olefin-silane system. The best mode of practice is to introduce the amine with the olefin and not with the alkoxysilane; although the amine can be introduced with the silane.

Promotion by amines is effective for those hydrosilation products which can be purified, as by distillation, and thusly separated from the amines, which may be lower or higher boilers which will be stripped or remain in the distillation residue, and can be isolated for disposal, or reused to promote a subsequent batch of product.

EXAMPLES

The following illustrative and comparative examples are intended to describe the present invention in more detail; however, they are not meant to limit the scope of the specification and claims. All parts and percentages presented in the examples below are by weight unless otherwise specified. The abbreviations g, mL, VCMX, AGE, TVC, CPA, $Pt_2(M*M*)_3$ solution, Si-H, AcOH, MeOH, EtOH, and GC stand for gram, milliliter, 4-vinylcyclohexene monoxide, allyl glycidyl ether, a mixture of three structural isomers of trivinylcyclohexane, solution consisting of 10% (wt/wt) of hexachloroplatinic acid in ethanol, a solution of 12% (wt/wt) of tris(tetramethyldivinyldisiloxane)diplatinum (0), any silicon hydride-containing species, acetic acid, methanol, ethanol, and gas chromatography, respectively. An internal standard was used in order to determine the percent of uneluted heavies for the GC analysis for those examples with VCMX. Uneluted heavies are defined as all components that did not elute under the GC conditions employed for the specific analysis. An * indicates no internal standard was used.

EXAMPLES OF THE INVENTION

General Procedure for the Reaction of an Olefin and an Alkoxysilane.

1.) In the presence of an excess of olefin. A typical reaction was conducted by treating 1.05 to 1.30 molar equivalents (vs. an alkoxysilane) of an olefin at room temperature, an amine and platinum precatalyst or a precatalyst solution. This solution was warmed. At 90 ° C., the solution was treated with 1.00 molar equivalent of an alkoxysilane. The addition of the alkoxysilane resulted in an exothermic reaction. The temperature of the solution was maintained between 90–100° C. throughout the silane addition. After the alkoxysilane addition was completed, the solution's temperature was maintained at 90° C. for one hour. After this time, solution was allowed to cool to room temperature. An aliquot of the crude reaction was analyzed by GC.

2.) In the presence of an excess of alkoxysilane. A typical reaction was conducted by treating 1.05 to 1.30 molar equivalents an alkoxysilane (versus the desired olefin) at room temperature with an amine and platinum precatalyst or a precatalyst solution. The amine can be dissolved either in the alkoxysilane or the olefin. This solution was warmed to ~80° C. (refluxing $(MeO)_3SiH$), and treated with 1.00 molar equivalent of the desired olefin (or olefin-amine solution). The addition of olefin (or olefin-amine solution) resulted in an exothermic reaction. The solution's temperature was maintained between 90–100° C. throughout the olefin's addition. After the olefin addition was completed, the solution's temperature was maintained at 90° C. for one hour. After this time, the solution was allowed to cool to room temperature. An aliquot of This solution was analyzed by GC.

Comparative Example 1

At room temperature, 20.00 g of neat 1-octene was treated with 0.010 ml of CPA and warmed. At 90° C., the 1-octene solution was treated with 19.10 g of $Cl_3SiH$. After the $Cl_3SiH$ addition was completed, the solution was maintained at 90° C. for one hour. This solution was analyzed by GC.

| $Cl_3SiH$ | $Cl_4Si$ | 1-Octene | Octene isomers | Product |
|---|---|---|---|---|
| 6.32 | 0.42 | 0.1 | 2.20 | 89.11 |

Comparative Example 2

At room temperature, 20.00 g of neat 1-octene was treated with 0.010 ml of CPA and warmed. At 90° C., the 1-octene solution was treated with 18.00 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | 1-Octene | Octene isomers | Product |
|---|---|---|---|---|
| 12.8 | 0.2 | 66.2 | 3.8 | 15.9 |

Comparative Example 3

At room temperature, 20.00 g of neat 1-octene was treated with 0.019 ml of acetic acid, 0.010 ml of CPA and warmed. At 90° C., the 1-octene solution was treated with 18.00 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | 1-Octene | Octene isomers | Product |
|---|---|---|---|---|
| 0.1 | 0.3 | 1.9 | 8.0 | 87.6 |

Example 1

At room temperature, 20.00 g of neat 1-octene was treated with 0.020 ml of aniline, 0.010 ml of CPA and warmed. At 90° C., the 1-octene solution was treated with 18.00 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | 1-Octene | Octene isomers | Product |
|---|---|---|---|---|
| 0.1 | 0.3 | 8.4 | 5.5 | 83.8 |

For examples 2–8, all reactions were conducted using a 20% molar excess of 1-octene (98% purity) versus $(MeO)_3SiH$, an amine promoter and 10 ppm Pt as a solution of chloroplatinic acid at 90° C. followed by one hour at 90° C. after the addition was completed. All solutions were analyzed using gas chromatography. The GC data for Examples 2–8 are summarized in Table 1.

TABLE 1

The effect of amines on the Pt-catalyzed, amine-promoted hydrosilation reaction of 1-octene.[a]

| Examples | Amine Promoters | $(MeO)_3SiH$ | $(MeO)_4Si$ | 1-Octene | Octene isomers[b] | Product |
|---|---|---|---|---|---|---|
| 2 | 1000 ppm phenothiazine | 8.8 | 0.4 | 54.8 | 6.5 | 28.4 |
| 3 | 640 ppm $NH[Si(CH_3)_3]_2$ | 6.2 | 0.9 | 41.4 | 5.2 | 44.9 |
| 4 | 600 ppm diphenylamine | 10.4 | 1.2 | 59.1 | 6.3 | 21.4 |
| 5 | 800 ppm di(n-butyl)amine | 16.7 | 1.4 | 78.6 | 0.4 | 1.7 |
| 6 | 640 ppm $NH(t\text{-butyl})[Si(CH_3)_3]$ | 12.8 | 1.1 | 75.6 | 1.3 | 8.6 |
| 7 | 640 ppm $N(CH_3)[Si(CH_3)_3]_2$ | 8.4 | 1.6 | 40.6 | 7.6 | 40.1 |
| 8 | 640 ppm $N[Si(CH_3)_3]_3$ | 10.5 | 1.2 | 46.4 | 9.7 | 28.1 |

[a]All reactions were conducted at 90° C. using 20% mole excess of 1-octene (98% purity) and 10 ppm Pt (CPA).
[b]This value is the sum of the three isomers of octene observed.

Example 9

At room temperature, 20.68 g of neat VCMX was treated with 0.020 g of aniline, 0.018 ml of CPA and warmed. At 90° C., the VCMX solution was treated with 18.43 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | VCMX | VCMX Isomer | Product | Uneluted Heavies |
|---|---|---|---|---|---|
| 0.1 | 1.9 | 1.6 | 3.8 | 85.3 | 3.5 |

For Examples 10–17, all reactions were conducted using a 10% molar excess of VCMX (97% purity) versus $(MeO)_3SiH$, an amine promoter and 10 ppm Pt as a solution of chloroplatinic acid at 90° C. followed by one hour at 90° C. after the addition was completed. All solutions were analyzed using gas chromatography. The GC data for Examples 10–17 are summarized in Table 2.

TABLE 2

GC data for the platinum-catalyzed, amine-promoted hydrosilation reaction of VCMX and TMS.[a]

| Examples | Amine Promoters | $(MeO)_3SiH$ | $(MeO)_4Si$ | VCMX | VCMX Isomer | Product | Uneluted Heavies |
|---|---|---|---|---|---|---|---|
| 10 | 500 ppm aniline | 0.1 | 1.9 | 1.6 | 3.8 | 85.3 | 3.5 |
| 11 | 500 ppm p-anisidine | 0.1 | 1.0 | 4.6 | 0.9 | 88.4 | 1.2 |
| 12 | 500 ppm 4- | 0.1 | 1.3 | 1.3 | 5.1 | 87.6 | 0.8 |
| 13 | 500 ppm benzyl amine | 0.1 | 0.8 | 1.9 | 2.44 | 84.9 | 7.8 |
| 14 | 640 ppm $NH[Si(CH_3)_3]_2$ | 0.1 | 0.5 | 3.4 | 1.1 | 92.2 | 1.0 |
| 15 | 500 ppm pyridine | 46.5 | 0.3 | 50.6 | 1.4 | 0.1 | 0.1 |
| 16 | 500 ppm phenothiazine | 29.1 | 0.7 | 30.4 | 1.1 | 21.9 | 14.5 |
| 17 | 500 ppm triethylamine | 31.8 | 6.8 | 39.7 | 0.1 | 15.3 | 0.9 |

[a]All reactions were conducted using a 10% mole excess of VCMX (97%) vs. $(MeO)_3SiH$ (99%) and 10 ppm Pt (CPA). No additional gelation inhibitor or promoter was used.

Comparative Example 4

At room temperature, 20.07 g of neat AGE was treated with 0.010 ml of CPA and warmed. At 90° C., the AGE solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | AGE | AGE isomers | β-isomer | γ-isomer |
|---|---|---|---|---|---|
| 5.7 | 0.8 | 13.4 | 7.4 | 0.8 | 63.2 |

Example 18

At room temperature, 20.10 g of neat AGE was treated with 0.020 g of phenothiazine, 0.010 ml of CPA and warmed. At 90° C., the AGE solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | AGE | AGE isomers | β-isomer | γ-isomer |
|---|---|---|---|---|---|
| 5.4 | 0.8 | 13.4 | 7.4 | 0.8 | 63.2 |

Example 19

At room temperature, 20.10 g of neat AGE was treated with 0.025 mL of $NH[Si(CH_3)_3]_2$, 0.010 ml of CPA and warmed. At 90° C., the AGE solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | AGE | AGE isomers | β-isomer | γ-isomer |
|---|---|---|---|---|---|
| 5.4 | 1.5 | 1.0 | 10.0 | 1.0 | 77.1 |

For example 20–22, all reactions were conducted using a 20% molar excess of AGE (99% purity) versus $(MeO)_3SiH$, an amine promoter and 10 ppm Pt as a solution of chloroplatinic acid at 90° C. followed by one hour at 90° C. after the addition was completed. All solutions were analyzed using gas chromatography. The GC data for comparative Example 4 and Examples 18–22 are summarized in Table 3.

TABLE 3

GC data for the hydrosilation reaction of trimethoxysilane and AGE.[a]

| Examples | Amine Promoters | $(MeO)_3SiH$ | $(MeO)_4Si$ | AGE | AGE isomers | β-isomer | γ-isomer |
|---|---|---|---|---|---|---|---|
| CE4 | Control | 5.7 | 0.8 | 13.4 | 7.4 | 0.8 | 63.2 |
| 18 | 500 ppm phenothiazine | 5.4 | 1.5 | 1.0 | 10.0 | 1.0 | 77.1 |
| 19 | 640 ppm $NH[Si(CH_3)_3]_2$ | 2.1 | 1.8 | 0.8 | 9.8 | 1.1 | 76.4 |
| 20 | 500 ppm acetic acid | 0.1 | 0.3 | 6.0 | 11.2 | 0.5 | 79.8 |
| 21 | 500 ppm pyridine | 35.1 | 1.6 | 44.8 | 1.1 | 0.1 | 12.3 |
| 22 | 500 ppm triethylamine | 3.1 | 41.4 | 50.8 | 0.2 | 0.1 | 0.2 |

[a]All reactions were conducted at 90° C. using a 20% mole excess of AGE (99%) and 10 ppm Pt (CPA).

Comparative Example 5

At room temperature, 19.80 g of neat $(MeO)_3SiH$ was treated with 0.016 ml of $Pt_2(M^*M^*)_3$ and warmed. At ~85° C., the TMS solution was treated with 20.02 g of N-allylaniline. After the N-allylaniline addition was completed, the solution was maintained at 90° C. or one hour. This solution was analyzed by GC.

| $(MeO)_3SiH$ | $(MeO)_4Si$ | N-allylaniline | N-propylaniline | β-isomer | γ-isomer |
|---|---|---|---|---|---|
| 4.2 | 2.3 | 2.0 | 1.7 | 23.6 | 59.4 |

Example 23

At room temperature, 19.80 g of neat $(MeO)_3SiH$ was treated with 0.40 g of aniline, 0.016 ml of $Pt_2(M^*M^*)_3$ and warmed. At ~85° C., the $(MeO)_3SiH$ solution was treated with 20.02 g of N-allylaniline. After the N-allylaniline addition was completed, the solution was maintained at 90° C. for one hour. This solution was analyzed by GC.

| $(MeO)_3SiH$ | $(MeO)_4Si$ | N-allylaniline | N-propylaniline | β-isomer | γ-isomer |
|---|---|---|---|---|---|
| 5.4 | 1.1 | 1.1 | 0.8 | 2.1 | 82.1 |

Example 24

At room temperature, 19.80 g of neat $(MeO)_3SiH$ was treated with 0.016 ml of $Pt_2(M^*M^*)_3$ and warmed. At ~85° C., the $(MeO)_3SiH$ solution was treated with a solution consisting of 0.40 g of aniline dissolved in 20.02 g of N-allylaniline. After the N-allylaniline addition was completed, the solution was maintained at 90° C. for one hour. This solution was analyzed by GC.

| $(MeO)_3SiH$ | $(MeO)_4Si$ | N-allylaniline | N-propylaniline | β-isomer | γ-isomer |
|---|---|---|---|---|---|
| 0.1 | 1.7 | 1.0 | 0.6 | 0.6 | 84.1 |

For examples 25–28, all reactions were conducted using a 10% molar excess of $(MeO)_3SiH$ versus N-allylaniline (97% purity), an amine promoter and 20 ppm Pt as a solution of $[Pt_2(M^*M^*)_3]$ at 85° C. followed by one hour at 90° C. after the addition was completed. All solutions were analyzed using gas chromatography. The GC data for Comparative Example 5 and Examples 23–28 are summarized in Table 4.

TABLE 4

GC data for the hydrosilation reaction of N-allylaniline.[a]

| Examples | Amine Promoters | $(MeO)_3SiH$ | $(MeO)_4Si$ | N-allylaniline | N-propylaniline | β-isomer | γ-isomer |
|---|---|---|---|---|---|---|---|
| CE5 | Control | 4.2 | 2.3 | 2.0 | 1.7 | 23.6 | 59.4 |
| 23 | 1.0% aniline in $(MeO)_3SiH$ | 5.4 | 1.1 | 1.1 | 0.8 | 2.1 | 82.1 |
| 24 | 1.0% aniline in N-allylaniline | <0.1 | 1.7 | 1 | 0.6 | 0.6 | 84.1 |
| 25 | 1.0% N,N-dimethylaniline | 2.2 | 0.6 | 7.0 | 1.3 | 16.7 | 57.6 |
| 26 | 1.0% pyridine | 2.6 | 0.6 | 1.4 | 4.6 | 4.1 | 60.1 |
| 27 | 500 ppm benzylamine | 8.7 | 0.3 | 82.6 | <0.1 | 0.1 | 4.6 |
| 28 | 500 ppm phenothiazine | 6.0 | 0.5 | 34.5 | 1.7 | 6.4 | 39.8 |

[a]All reactions were conducted at 85° C. a 10% mole excess of $(MeO)_3SiH$ versus N-allylaniline using 20 ppm Pt $[Pt_2(M^*M^*)_3]$ and the amine was dissolved in the N-allylaniline.

Comparative Example 6

At room temperature, 12.10 g of neat TVC was treated with 0.010 ml of CPA and warmed. At 90° C., the TVC solution was treated with 19.80 g of $(MeO)_3SiH$. After the $(MeO)_3SiH$ addition was completed, the solution was maintained at 90° C. for one hour. This solution was analyzed by GC.

| | | | Product (Si:TVC ratio) | | |
|---|---|---|---|---|---|
| $(MeO)_3SiH$ | $(MeO)_4Si$ | TVC | 1:1 | 2:1 | 3:1 |
| 19.0 | 0.6 | 34.1 | 39.5 | 6.7 | 0.1 |

Example 29

At room temperature, 12.10 g of neat TVC was treated with 0.016 g of aniline, 0.010 ml of CPA and warmed. At 90° C., the TVC solution was treated with 19.8 g of (MeO)$_3$SiH. After the (MeO)$_3$SiH addition was completed, the solution was maintained at 90° C. for one hour. This solution was analyzed by GC.

|  |  |  | \multicolumn{3}{c}{Product (Si:TVC ratio)} | | |
|---|---|---|---|---|---|
| (MeO)$_3$SiH | (MeO)$_4$Si | TVC | 1:1 | 2:1 | 3:1 |
| 7.5 | 0.9 | 0.4 | 0.6 | 27.0 | 63.3 |

Example 30

At room temperature, 12.10 g of neat TVC was treated with 0.032 g of aniline, 0.010 ml of CPA and warmed. At 90° C., the TVC solution was treated with 19.8 g of (MeO)$_3$SiH. After the (MeO)$_3$SiH addition was completed, the solution was maintained at 90° C. for two hours. This solution was analyzed by GC.

|  |  |  | \multicolumn{3}{c}{Product (Si:TVC ratio)} | | |
|---|---|---|---|---|---|
| (MeO)$_3$SiH | (MeO)$_4$Si | TVC | 1:1 | 2:1 | 3:1 |
| 4.2 | 3.3 | 0.1 | 0.1 | 7.3 | 77.4 |

For examples 31–36, all reactions were conducted using a 10% molar excess of (MeO)$_3$SiH versus TVC, an amine promoter and 10 ppm Pt as a solution of chloroplatinic acid at 90° C. followed by one hour at 90° C. after the addition was completed. All solutions were analyzed using gas chromatography. The GC data for Examples 29–36 are summarized in Table 5.

TABLE 5

GC data for the hydrosilation reaction of TVC.[a]

| Examples | Amine Promoters | (MeO)$_3$SiH | (MeO)$_4$Si | TVC | Product (Si:TVC ratio) | | |
|---|---|---|---|---|---|---|---|
|  |  |  |  |  | 1:1 | 2:1 | 3:1 |
| CE6 | Control | 19.0 | 0.6 | 34.1 | 39.5 | 6.7 | 0.1 |
| 29 | 500 ppm aniline | 7.5 | 0.9 | 0.4 | 0.6 | 25.3 | 63.3 |
| 30 | 1000 ppm aniline | 7.2 | 3.6 | 0.2 | 0.6 | 13.1 | 72.0 |
| 31 | 500 ppm acetic acid | 17.8 | 1.1 | 2.6 | 22.9 | 42.5 | 9.6 |
| 32 | 500 ppm N,N-dimethylaniline | 14.5 | 0.1 | 36.9 | 38.1 | 6.7 | 0.1 |
| 33 | 500 ppm phenothiazine | 16.1 | 0.1 | 59.4 | 24.6 | 0.1 | 0.1 |
| 34 | 500 ppm triethylamine | 20.5 | 1.1 | 58.1 | 20.2 | 0.1 | 0.1 |
| 35 | 500 ppm pyridine | 29.5 | 1.1 | 50.7 | 15.1 | 1.2 | 0.1 |
| 36 | 640 ppm NH[Si(CH$_3$)$_3$]$_2$ | 12.3 | 1.3 | 0.5 | 14.8 | 51.5 | 18.6 |

[a]All reactions were conducted at 90 °C. using a 10% mole excess of TMS versus TVC using 10 ppm Pt (CPA).

Comparative Example 7

At room temperature, 12.10 g of neat TVC was treated with 0.010 ml of CPA and warmed. At 90° C., the methyldiethoxysilane solution was treated with 19.8 g of TVC solution containing 0.020 ml of aniline. After the TVC addition was completed, the solution was maintained at 90° C. for one hour. This solution was analyzed by GC.

|  |  |  | \multicolumn{3}{c}{Product (Si:TVC ratio)} | | |
|---|---|---|---|---|---|
| (EtO)$_2$MeSiH | (EtO)$_3$MeSi | TVC | 1:1 | 2:1 | 3:1 |
| 7.4 | 2.6 | 0.1 | 0.1 | 5.4 | 80.1 |

For examples 37–38, all reactions were conducted using a 10% molar excess of Me(EtO)$_2$SiH versus TVC, an amine promoter and 10 ppm Pt as a solution of chloroplatinic acid at 90° C. followed by one hour at 90° C. after the addition was completed. All solutions were analyzed using gas chromatography. The GC data for comparative Example 7 and Examples 37–38 are summarized in Table 6.

TABLE 6

GC data for the hydrosilation reaction of 1,2,4-trivinylcyclohexane (TVC).[a]

| | | | | | Product (Si:TVC ratio) | | |
|---|---|---|---|---|---|---|---|
| Examples | Amine Promoters | $(EtO)_2MeSiH$ | $(EtO)_3MeSi$ | TVC | 1:1 | 2:1 | 3:1 |
| CE7 | Control° | 7.4 | 2.6 | 0.1 | 0.1 | 5.4 | 80.1 |
| 37 | 1000 ppm aniline | 6.7 | 2.6 | 3.2 | 0.1 | 0.1 | 87.0 |
| 38 | 640 ppm $NH[Si(CH_3)_3]_2$ in TVC | 1.2 | 1.9 | 0.5 | 4.9 | 15.3 | 74.5 |

[a]All reactions were conducted at 90° C. using a 10% mole excess of $Me(EtO)_2SiH$ using 10 ppm Pt (CPA).

Comparative Example 8

At room temperature, 6.50 g of neat TVC was treated with 0.007 ml of CPA and warmed. At 90° C., the TVC solution was treated with 24.48 g of $(EtO)_3SiH$ solution. After the $(EtO)_3SiH$ addition was completed, the solution was maintained at 90° C. for 2 hours. This solution was analyzed by GC.

| | | | Product (Si:TVC ratio) | | |
|---|---|---|---|---|---|
| $(EtO)_3SiH$ | $(EtO)_4Si$ | TVC | 1:1 | 2:1 | 3:1 |
| 46.8 | 1.5 | 2.9 | 25.6 | 16.5 | 0.5 |

Example 39

At room temperature, 6.50 g of neat TVC was treated with 0.007 ml of CPA, 0.031 mL of aniline and warmed. At 90° C., the $(EtO)_3SiH$ solution was treated with 24.48 g of $(EtO)_3SiH$. After the $(EtO)_3SiH$ addition was completed, the solution was maintained at 90° C. for 2 hours. This solution was analyzed by GC.

| | | | Product (Si:TVC ratio) | | |
|---|---|---|---|---|---|
| $(EtO)_3SiH$ | $(EtO)_4Si$ | TVC | 1:1 | 2:1 | 3:1 |
| 16.1 | 2.4 | 0.1 | 0.1 | 13.2 | 65.9 |

Comparative Example 9

At room temperature, 31.51 g of neat eugenol methyl ether was treated with 0.010 ml of CPA and warmed. At 90° C., the eugenol methyl ether solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Eugenol methyl ether | Eugenol methyl ether Isomer | Product |
|---|---|---|---|---|
| 3.9 | 0.1 | 25.8 | 18.5 | 49.4 |

Comparative Example 10

At room temperature, 31.51 g of neat eugenol methyl ether was treated with 0.025 g of acetic acid, 0.010 ml of CPA and warmed. At 90° C., the eugenol methyl ether solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Eugenol methyl ether | Eugenol methyl ether Isomer | Product |
|---|---|---|---|---|
| 0.2 | 0.1 | 25.8 | 10.6 | 47.5 |

Example 40

At room temperature, 31.51 g of neat eugenol methyl ether was treated with 0.025 g of benzylamine, 0.010 ml of CPA and warmed. At 90° C., the eugenol methyl ether solution was treated with 18.0 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Eugenol methyl ether | Eugenol methyl ether isomers | Product |
|---|---|---|---|---|
| 0.3 | 0.7 | 1.2 | 9.7 | 75.0 |

For examples 41–44, all reactions were conducted using a 20% molar excess of eugenol methyl ether versus $(MeO)_3SiH$, an amine promoter and 10 ppm Pt as a solution of chloroplatinic acid at 90° C. followed by one hour at 90° C. after the addition was completed. All solutions were analyzed using gas chromatography. The GC data for Comparative Examples 9 and 10 and Examples 40–44 are summarized in Table 7.

TABLE 7

GC data for the hydrosilation reaction of eugenol methyl ether.[a]

| Examples | Amine Promoters | $(MeO)_3SiH$ | $(MeO)_4Si$ | Eugenol Methyl Ether | isomers | Product |
|---|---|---|---|---|---|---|
| CE9 | Control | 3.9 | <0.1 | 25.8 | 18.5 | 49.4 |
| CE10 | 500 ppm acetic acid | 0.2 | 0.1 | 25.8 | 10.6 | 47.5 |
| 40 | 500 ppm benzyl amine | 0.3 | 0.7 | 1.2 | 9.7 | 75.0 |
| 41 | 500 ppm aniline | 15.5 | 0.2 | 12.0 | 5.0 | 66.2 |
| 42 | 500 ppm phenothiazine | 5.2 | 0.2 | 41.7 | 12.3 | 38.7 |
| 43 | 500 ppm 2-methoxybenzylamine | 2.2 | 1.8 | 30.7 | 6.0 | 58.0 |
| 44 | 500 ppm triethylamine | 4.9 | <0.1 | 32.6 | 6.3 | 55.1 |

[a]All reactions were conducted at 90 °C. using a 20% mole excess of eugenol methyl ether and 10 ppm Pt (CPA).

Comparative Example 11

At room temperature, 107.78 g of neat hexadecene was treated with 0.440 ml of CPA and warmed. At 90° C., the hexadecene solution was treated with 48.9 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Hexadecene | Hexadecene isomers | Product |
|---|---|---|---|---|
| 5.4 | 0.5 | 52.2 | 12.5 | 23.6 |

Comparative Example 12

At room temperature, 36.6 g of neat hexadecene was treated with 0.112 g of acetic acid, 0.017 ml of CPA and warmed. At 90° C., the hexadecene solution was treated with 22.3 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Hexadecene | Hexadecene isomers | Product |
|---|---|---|---|---|
| 2.9 | 0.4 | 10.4 | 10.8 | 68.2 |

Example 45

At room temperature, 36.7 g of neat hexadecene was treated with 0.081 g of aniline, 0.012 ml of $Pt_2(M^*M^*)_3$ and warmed. At 90° C., the hexadecene solution was treated with 18.6 g of $(MeO)_3SiH$. After the $(MeO)_3SiH$ addition was completed, the solution was maintained at 90° C. for one hour. This solution was analyzed by GC.

| $(MeO)_3SiH$ | $(MeO)_4Si$ | Hexadecene | Hexadecene isomers | Product |
|---|---|---|---|---|
| 0.2 | 0.5 | 0.7 | 3.9 | 86.28 |

What is claimed is:

1. A process comprising reacting hydridoalkokysilane with (b) olefin in the presence of (c) platinum catalyst and (d) a weakly nucleophilic amine of the formula $NZ^1Z^2Z^3$ wherein $Z^1$ is an aryl, alkaryl, or aralkyl group of $C_6$ to $C_{20}$ carbon atoms, or an organosilyl substituent of the formula $SiR_3$, wherein R is an alkyl of $C_1$ to $C_{20}$ or an aryl of $C_6$ to $C_{10}$, $Z^2$ is hydrogen, alkyl of $C_1$ to $C_{20}$, an aryl, alkaryl, or aralkyl group of $C_6$ to $C_{20}$ carbon atoms, or $SiR_3$, wherein R is as previously defined; $Z^3$ is the same as $Z^1$ or $Z^2$, and, optionally, two of $Z^1$, $Z^2$ and $Z^3$ taken together with the nitrogen atom form an aromatic heterocyclic ring.

2. The process according to claim 1 wherein the hydridoalkoxysilane corresponds to the formula $R_nX_{3-n}SiH$ wherein R is a branched or linear alkyl group of 1 to 18 carbon atoms, a cyclic alkyl group of four to eight carbon atoms or an aryl, alkaryl, or aralkyl group of six to twelve carbon atoms, optionally containing halogen, oxygen, or nitrogen substituents with the proviso that such substituents do not interfere with either hydrosilation or promotion, and X is -OR, wherein R is as defined above, and n is 0, 1 or 2.

3. The process according to claim 2 wherein n is 0 or 1, and X is selected from the group consisting of ethoxy and methoxy.

4. The process according to claim 2 wherein the hydridoalkoxysilane is selected from the group consisting of trimethoxysilane, triethoxysilane, tri-n-propoxysilane, triisopropoxysilane, methyldimethoxysilane, methyldiethoxysilane, dimethylmethoxysilane, and dimethylethoxysilane.

5. The process according to claim 2 wherein the hydridoalkoxysilane is selected from the group consisting of trimethoxysilane and triethoxysilane.

6. The process according to claim 1 wherein the olefin is selected from the group consisting of alkenes, vinyl-group containing compounds and allylic-group containing compounds.

7. The process according to claim 1 wherein the olefin is selected from the group consisting of ethylene, propylene, butene, pentene, hexene, octene, hexadecene, octadecene, trivinylcyclohexene, 2-methylpropene, 2-methylbutene, diisobutylene, tertiary amylene, 2-butene, vinylcyclohexene monoxide, allyl glycidyl ether, allyl esters, allyl polyethers, allylic tertiary amines, and methallyl derivatives thereof, N-allylaniline, N,N-dimethallylamine, N-ethylmethallylamine, vinyl esters and ethers, vinylsilanes, acrylates and methacrylates.

8. The process according to claim 1 wherein the olefin is selected from the group consisting of ethylene, propylene, butene, pentene, hexene, octene, hexadecene, octadecene, trivinylcyclohexene, 2-methylpropene, 2-methylbutene and diisobutylene.

9. The process according to claim 1 wherein the platinum catalyst is chloroplatinic acid.

10. The process according to claim 1 wherein the weakly nucleophilic amine is used at a level of 25 to 20,000 parts per million by weight of the combined weight of hydridoalkoxysilane and olefin.

11. The process according to claim 1 wherein the weakly nucleophilic amine is selected from the group consisting of aniline, hexamethyldisilazane, phenothiazine, aminonaphthalene, benzylamine, pyridine and derivatives thereof.

12. The process according to claim 1 wherein the olefin is an amino olefin.

13. The process according to claim 1 wherein the olefin is hexadecene.

14. The process according to claim 1 wherein the reaction is conducted at a temperature of from about ambient temperature up to about 150° C. and a pressure of about 0.2 to about 2.0 atmospheres.

15. The process according to claim 1 wherein a molar excess of olefin relative to the hydridoalkoxysilane is employed in the reaction.

* * * * *